(12) United States Patent
Annest et al.

(10) Patent No.: US 7,441,342 B2
(45) Date of Patent: Oct. 28, 2008

(54) SYSTEM AND METHOD FOR SIZING A HEART FOR TREATING CONGESTIVE HEART FAILURE

(75) Inventors: Lon Annest, Tacoma, WA (US); Rob O'Reilly, Lafayette, CA (US); Sing-Fatt Chin, Pleasanton, CA (US); Arthur Bertolero, Danville, CA (US)

(73) Assignee: CHF Technologies, Inc., Danville, CA (US)

( * ) Notice: Subject to any disclaimer, the term of this patent is extended or adjusted under 35 U.S.C. 154(b) by 652 days.

(21) Appl. No.: 11/116,600

(22) Filed: Apr. 27, 2005

(65) Prior Publication Data

US 2006/0030792 A1    Feb. 9, 2006

Related U.S. Application Data

(63) Continuation-in-part of application No. 10/826,028, filed on Apr. 16, 2004, now abandoned, and a continuation-in-part of application No. 10/785,486, filed on Feb. 24, 2004, which is a continuation of application No. 10/224,659, filed on Aug. 21, 2002, now Pat. No. 7,025,776, and a continuation-in-part of application No. 10/183,396, filed on Jun. 28, 2002, now Pat. No. 6,726,696, which is a continuation-in-part of application No. 10/127,714, filed on Apr. 23, 2002, now abandoned.

(60) Provisional application No. 60/626,251, filed on Nov. 8, 2004, provisional application No. 60/612,634, filed on Sep. 23, 2004, provisional application No. 60/612,633, filed on Sep. 23, 2004, provisional application No. 60/534,514, filed on Jan. 6, 2004, provisional application No. 60/518,270, filed on Nov. 5, 2003, provisional application No. 60/512,293, filed on Oct. 17, 2003, provisional application No. 60/500,762, filed on Sep. 4, 2003, provisional application No. 60/499,946, filed on Sep. 2, 2003, provisional application No. 60/488,292, filed on Jul. 18, 2003, provisional application No. 60/485,568, filed on Jul. 7, 2003, provisional application No. 60/466,653, filed on Apr. 29, 2003, provisional application No. 60/302,255, filed on Jun. 28, 2001, provisional application No. 60/300,892, filed on Jun. 25, 2001, provisional application No. 60/286,269, filed on Apr. 24, 2001.

(51) Int. Cl.
*A61B 5/103* (2006.01)
(52) U.S. Cl. ........................................ 33/512; 600/587
(58) Field of Classification Search ........... 33/511–512; 623/2.11; 600/587; 606/1, 232, 151, 102
See application file for complete search history.

(56) References Cited

U.S. PATENT DOCUMENTS 5,383,896 A    1/1995    Gershony (Continued)

*Primary Examiner*—Yaritza Guadalupe-McCall
(74) *Attorney, Agent, or Firm*—Townsend and Townsend and Crew LLP

(57) ABSTRACT

A method for use in reconstructing the left ventricle of the heart of a patient from a diseased state to an appropriate reconstructed state is disclosed. The method includes the steps of determining the body surface area of the patient; determining a characteristic of the left ventricle which is the same in the diseased state as in the reconstructed state; determining an appropriate sizer based on the determined body surface area of the patient and the characteristic of the left ventricle which is the same in the diseased state as in the reconstructed state; identifying akinetic tissue within a heart chamber wall; making an incision through the akinetic tissue in the chamber wall; inserting said appropriate sizer into the chamber through the incision; removing the sizer; and, closing the incision.

7 Claims, 15 Drawing Sheets

U.S. PATENT DOCUMENTS

| | | |
|---|---|---|
| 5,454,834 A | 10/1995 | Boebel |
| 5,645,568 A | 7/1997 | Chervitz |
| 5,797,960 A | 8/1998 | Stevens |
| 6,383,204 B1 | 5/2002 | Ferrera |
| 6,613,059 B2 | 9/2003 | Schaller |
| 6,681,773 B2 | 1/2004 | Murphy |
| 6,702,763 B2 | 3/2004 | Murphy |
| 6,716,234 B2 | 4/2004 | Grafton |
| 6,959,711 B2 | 11/2005 | Murphy |
| 6,994,093 B2 | 2/2006 | Murphy |
| 7,189,199 B2 | 3/2007 | McCarthy |
| 7,213,601 B2 * | 5/2007 | Stevens et al. .............. 33/512 |
| 2002/0133227 A1 | 9/2002 | Murphy |
| 2003/0045896 A1 | 3/2003 | Murphy |
| 2003/0050659 A1 | 3/2003 | Murphy |
| 2003/0181940 A1 | 9/2003 | Murphy |
| 2003/0187362 A1 | 10/2003 | Murphy |
| 2004/0064014 A1 | 4/2004 | Melvin |
| 2005/0020929 A1 | 1/2005 | Murphy |
| 2005/0096498 A1 * | 5/2005 | Houser et al. .............. 600/37 |
| 2005/0113810 A1 * | 5/2005 | Houser et al. ............. 606/151 |
| 2005/0113811 A1 * | 5/2005 | Houser et al. ............... 606/1 |
| 2005/0125012 A1 * | 6/2005 | Houser et al. ............. 606/148 |
| 2006/0247764 A1 * | 11/2006 | Annest et al. ............. 623/3.1 |

* cited by examiner

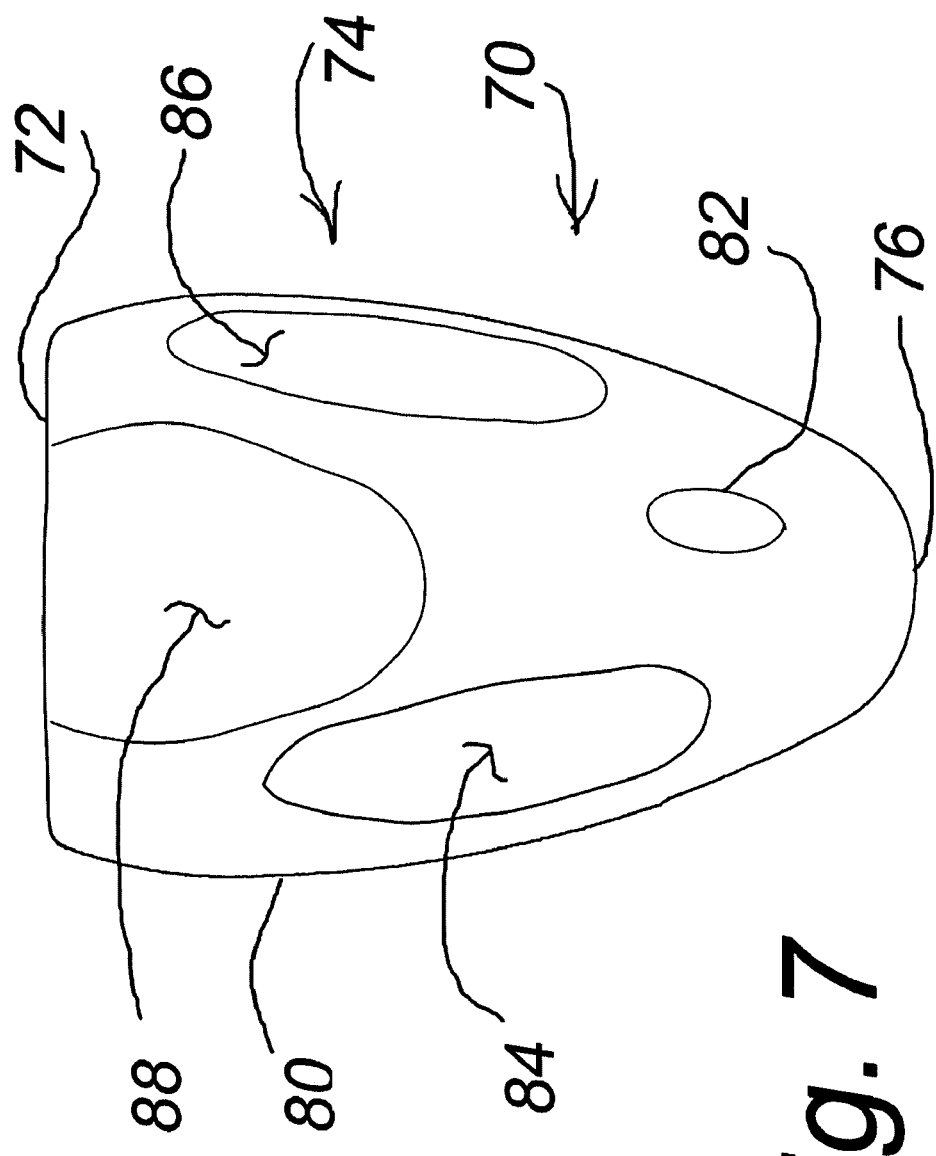

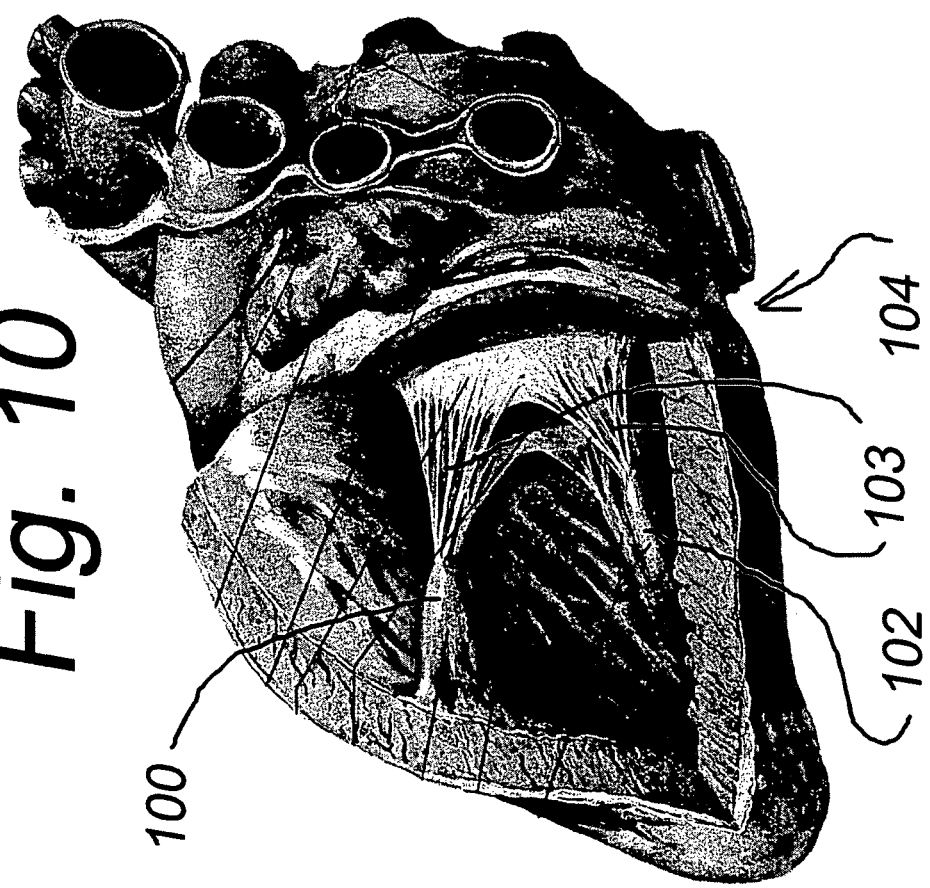

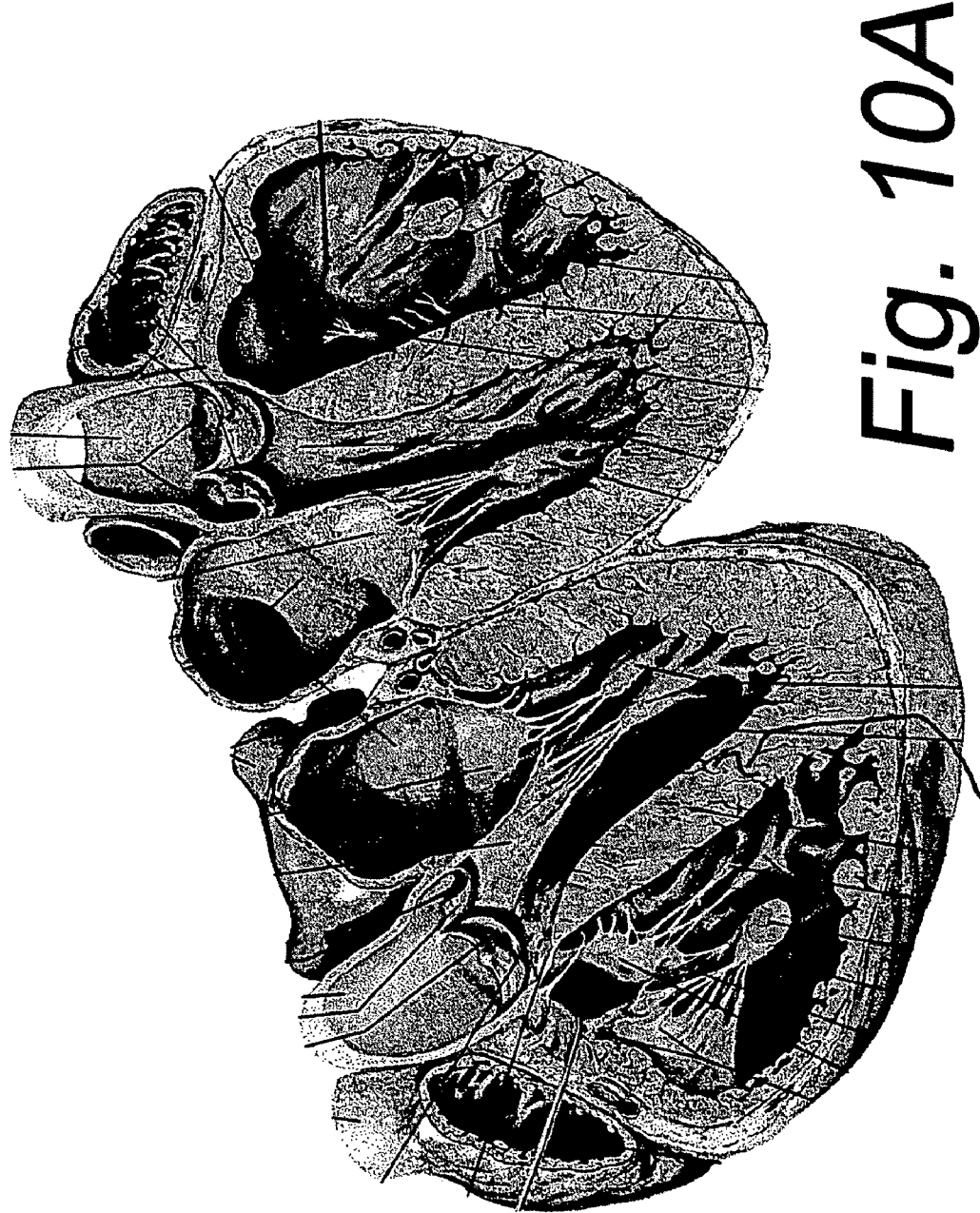

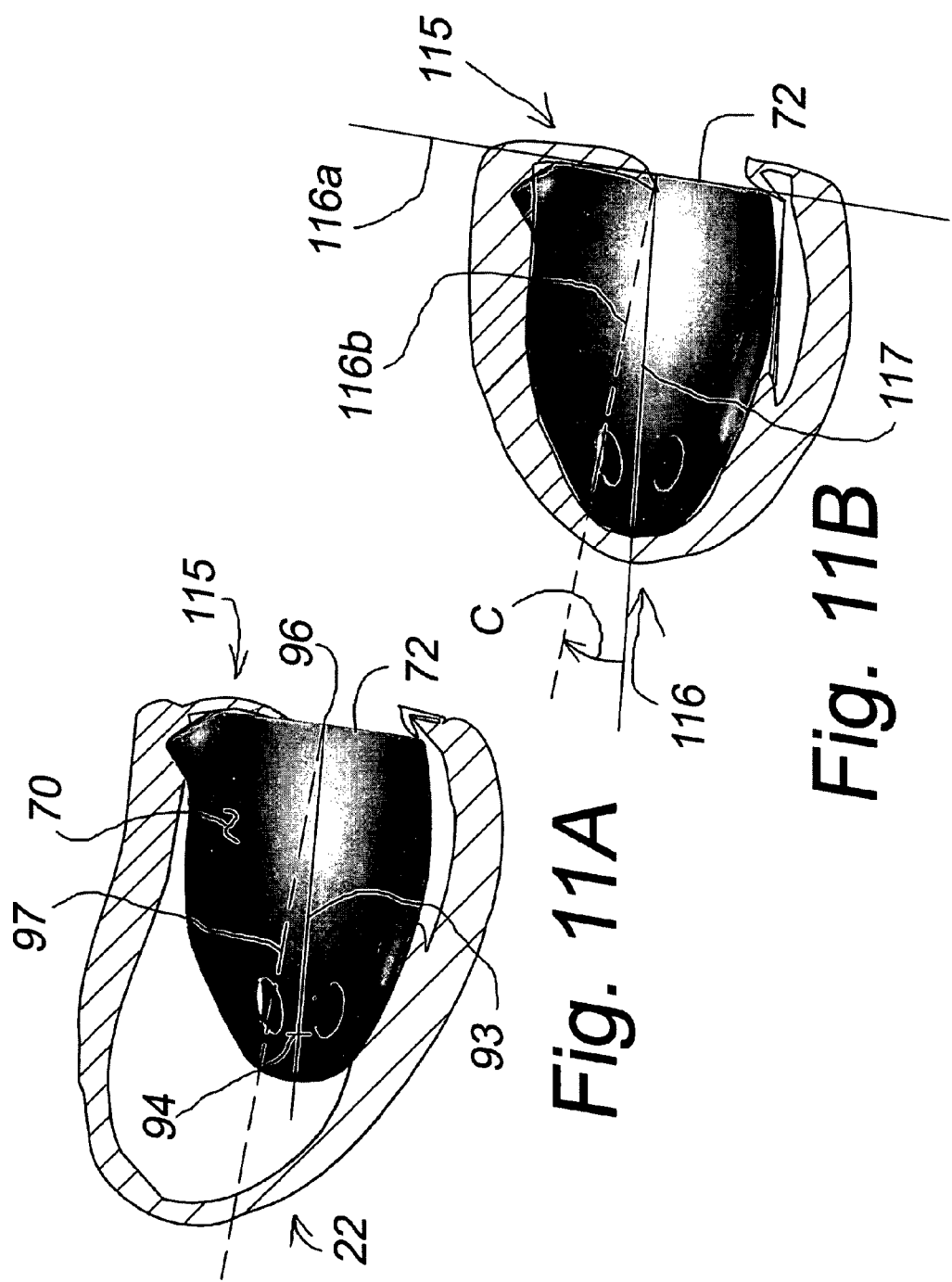

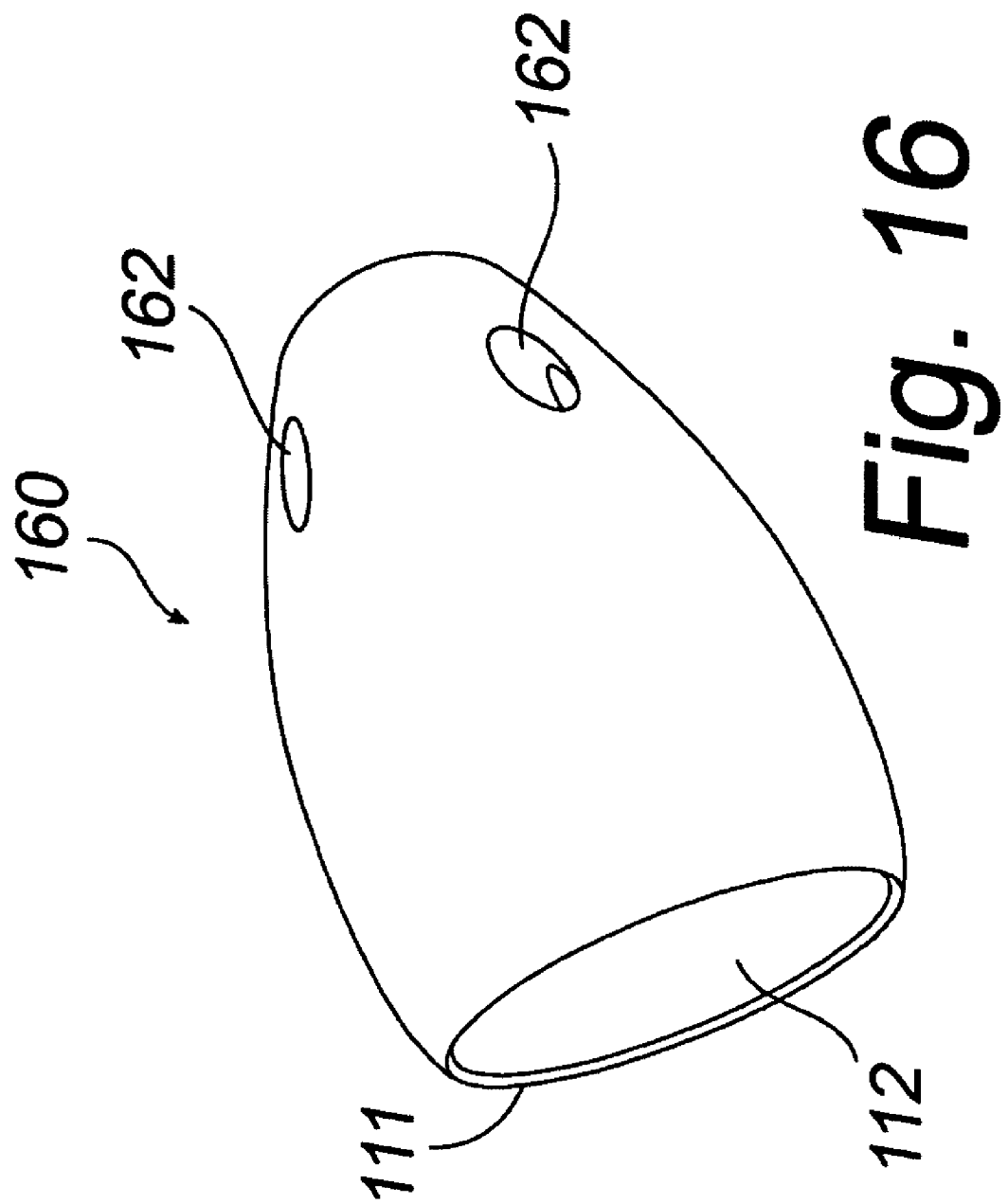

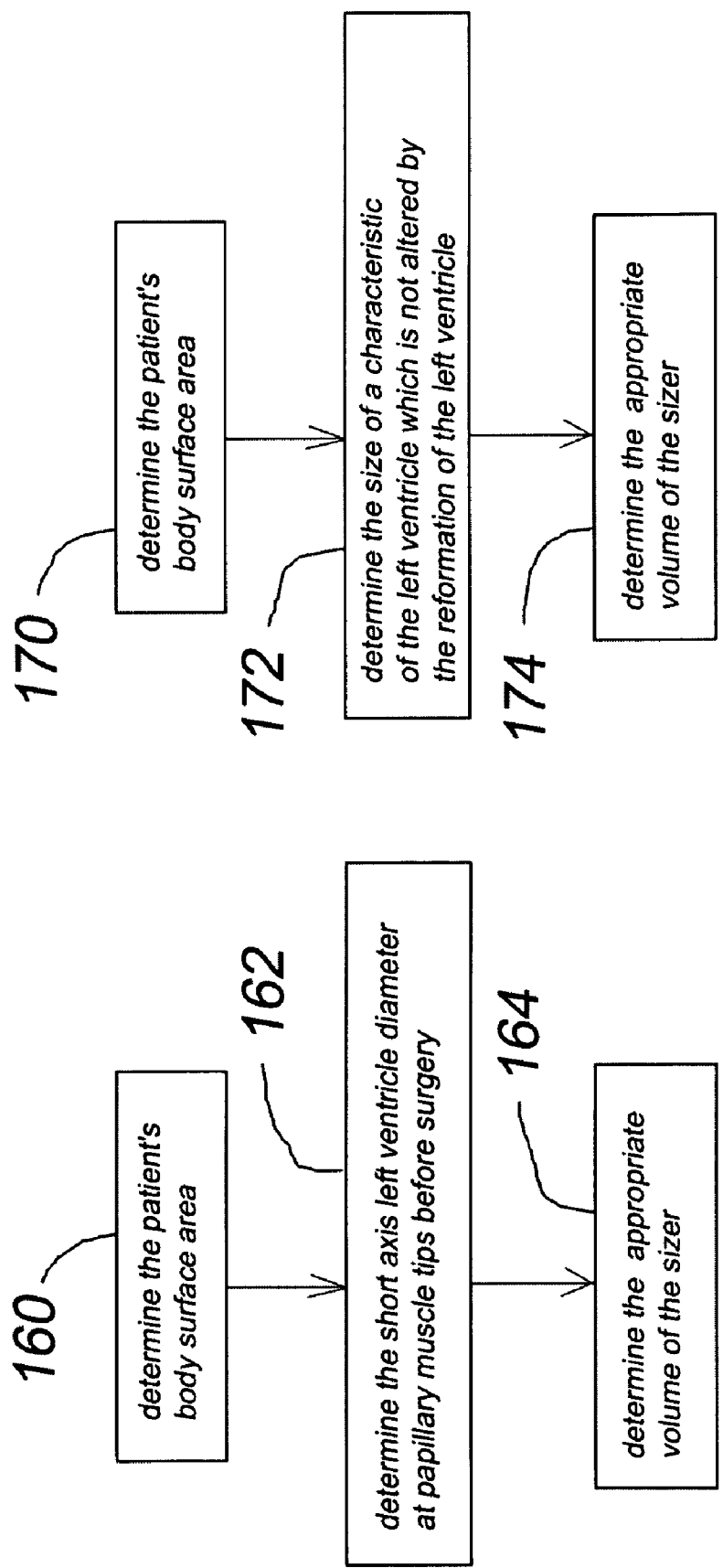

SYSTEM AND METHOD FOR SIZING A HEART FOR TREATING CONGESTIVE HEART FAILURE

RELATED APPLICATIONS

This application claims the benefit of the following U.S. Provisional Patent Applications which are incorporated herein in their entirety by reference: Ser. No. 60/612,633 filed Sep. 23, 2004, and titled "Device To Locate The Apex Of The Heart During Left Ventricular Restoration"; Ser. No. 60/612,634 filed Sep. 23, 2004, and titled "Method and Device for Determining the Appropriate Size for Left Ventricular Reconstruction"; and Ser. No. 60/626,251 filed Nov. 8, 2004 and titled "Method and Device for Determining Appropriate Volume for Left Ventricular Reconstruction (LVR)". This application also claims priority from and is a continuation-in-part of U.S. patent application Ser. No. 10/826,028, filed Apr. 16, 2004, now abandoned, and titled SIZING AND SHAPING DEVICE FOR TREATING CONGESTIVE HEART FAILURE, which claims priority to other patent applications. U.S. patent application Ser. No. 10/826,028 claims priority as follows: "This application claims priority from the following U.S. Provisional Patent Applications each of which is incorporated herein in its entirety by reference: Ser. No. 60/466,653, filed Apr. 29, 2003 and titled Ventricular Restoration; Ser. No. 60/485,568, filed Jul. 7, 2003 and titled Systems, Devices and Methods of Use for Treating Congestive Heart Failure (CHF); Ser. No. 60/488,292, filed Jul. 18, 2003 and titled Ventricular Sizing & Shaping Device and Method; Ser. No. 60/499,946, filed Sep. 2, 2003 and titled System and Method of Use to Employ Imaging Technology for Diagnosis, Measurement, Standardization, and Follow-up of Disease Processes and Determine Optimal Treatment; Ser. No. 60/500,762, filed Sep. 4, 2003 and titled Shaping Suture Device and Method of Use; Ser. No. 60/512,293, filed Oct. 17, 2003 and titled Less Invasive CHF Treatment—Reshaping the Heart; Ser. No. 60/518,270, filed Nov. 5, 2003 and titled Methods and Devices for Tracking Acute Myocardial Infarction; and Ser. No. 60/534,514, filed Jan. 6, 2004 and titled Squeeze Patch. This application also claims priority from and is a continuation-in-part from U.S. patent application Ser. No. 10/785,486, filed Feb. 24, 2004, and titled Patches and Collars for Medical Applications and Methods of Use, which claims priority from and is a continuation from U.S. patent application Ser. No. 10/224,659, filed Aug. 21, 2002 now U.S. Pat. No. 7,025,776 and titled Arteriotomy Closure Device and Techniques, which claims priority from U.S. Provisional Patent Application Ser. No. 60/286,269, filed Apr. 24, 2001 and titled Percutaneous Vessel Access Closure Device and Method; from U.S. Provisional Patent Application Ser. No. 60/300,892, filed Jun. 25, 2001 and titled Percutaneous Vessel Access Closure Device and Method; and from U.S. Provisional Patent Application Ser. No. 60/302,255, filed Jun. 28, 2001 and titled Percutaneous Vessel Access Closure Device and Method (Hemostatic Patch or Collar) each of which is incorporated herein in its entirety by reference. This application also claims priority from and is a continuation-in-part from U.S. patent application Ser. No. 10/183,396, filed Jun. 28, 2002 now U.S. Pat. No. 6,726,696 and titled Patches and Collars for Medical Applications and Methods of Use, which claims priority from and is a continuation-in-part from U.S. patent application Ser. No. 10/127,714, filed on Apr. 23, 2002, now abandoned, which claims priority from U.S. Provisional Patent Application No. 60/286,269, filed Apr. 24, 2001 and titled Percutaneous Vessel Access Closure Device and Method; from U.S. Provisional Patent Application Ser. No. 60/300,892, filed Jun. 25, 2001 and titled Percutaneous Vessel Access Closure Device and Method; and from U.S. Provisional Patent Application Ser. No. 60/302,255, filed Jun. 28, 2001 and titled Percutaneous Vessel Access Closure Device and Method (Hemostatic Patch or Collar), each of which is incorporated herein in its entirety by reference."

BACKGROUND OF THE INVENTION

1. Field of the Invention

The present invention relates to heart surgery.

2. Description of the Related Art

Congestive heart failure affects 5 million people in the United States, and the NIH reports that 550,000 new cases are diagnosed every year (U.S.). World-wide, the figure is estimated at 22 million. Death rates have grown at an almost exponential rate. Congestive heart failure is the most common discharge diagnosis among Americans over age 65.

Congestive heart failure is a clinical syndrome with heterogeneous etiologies including ischemic cardiomyopathy, valve dysfunction, hypertensive cardiomyopathy, chemotherapy, alcohol abuse, radiation injury, idiopathic conditions, and others. Therapy is directed at the underlying cause, such as coronary revascularization, valve replacement, bi-ventricular pacing, and extensive drug usage, leveled at both the source and the symptoms. Unfortunately, the collective results of all available therapies in the treatment of congestive heart failure are disappointing. Pharmacology and electrical resynchronization have improved the symptoms in many cases, but direct approaches to improving the function of the weakened heart muscle, the common thread in all cases, are few.

Congestive heart failure is a syndrome characterized by inadequate cardiac output, regardless of primary cause. One common cause of congestive heart failure is a previous heart attack causing "ischemia," or lack of oxygen to the heart tissue. Responsible for approximately two-thirds of congestive heart failure patients, ischemic cardiomyopathy follows a predictable course. Initially, there is an index event, most commonly an anterior myocardial infarction. When treated, the patient is stabilized, often receiving a balloon catheter dilitation, intra-coronary stent or bypass graft, and has an initially unremarkable recovery. However, over the next one to three years, a process known as "ventricular remodeling" takes place where the previously conical chamber becomes spherical and substantially dilated, and previously normal segments become acontractile. The syndrome of disabling, chronic, congestive heart failure begins. Drugs such as ARBs (angiotensin receptor blockers) and ACE (angiotensin converting enzyme) inhibitors have been shown to retard the progress of this disintegration of cardiac function, but the end result is delay, not cure.

One common symptom of many classes of heart disease is enlargement of the heart and/or dilation of the left ventricle. The cause of ventricular dilation is typically the result of a chronic volume overload or specific damage to the myocardium. If portions of the myocardium are damaged, increased requirements are put on the remaining healthy myocardium such that the heart may attempt to compensate with ventricular dilation and muscle hypertrophy. In diseased hearts, the compensation is not sufficient and the ventricular dilation and muscle hypertrophy progress to a point where efficiency of heart function begins to fall. Further attempts by the heart to compensate may accelerate this reduction in efficiency.

One surgical approach, the Dor Procedure (endoventricular circular patch plasty), has improved the course of the disease in selected congestive heart failure victims by excluding and reinforcing the dysfunctional, or akinetic, portion of the ventricle. That procedure typically involves the following steps:

Define the infarcted area on ventricular wall;
Incise through the infarcted area into the ventricle;
Open and secure the flaps of scarred ventricular tissue that were created during the incision;
Define the border around the viable and infarcted tissue in the ventricular wall; and
Place a Fontan stitch or purse-string suture around the circumferential margin where viable tissue meets the infarcted tissue and tighten the stitch like a noose, drawing the viable tissue closer together. (A second row of sutures may be required for further size reduction.)

Optionally, the Dor Procedure may also involve suturing a patch of material (typically woven or knitted Dacron®, but others can also be used) on the inside of the ventricle, eliminating the defect in the ventricular wall defined by the tightened purse-string or strings.

While the Dor Procedure has benefits, it also has disadvantages. First, it is difficult for surgeons using the procedure to resize the ventricle to its natural size. In addition, the Dor Procedure requires surgeons to estimate the appropriate ventricle size for a particular patient. Some surgeons inaccurately estimate the appropriate ventricle size resulting in a ventricle that is too small, which may leave the patient clinically worse than before the procedure.

Dr. Dor has attempted to decrease the likelihood of achieving the result of an inappropriately small ventricle through using a fluid filled balloon as a guide for the practitioner when drawing the tissue together. The use of a balloon, however, has not adequately solved the problem. First, the practitioner must still estimate the appropriate size for the ventricle in deciding how much to fill and expand the balloon. Second, the balloon has the added disadvantage that a needle or any other sharp object used during the procedure may rupture the balloon and render it useless for the remainder of the procedure.

In addition to the Dor procedure described above, various other surgical approaches have been developed to treat dilation of the left ventricle of the heart (and the resultant CHF), by primarily restoring the size and volume of the diseased heart. Paramount to restoring normal heart function is identification and reconstruction of the apex. Apical reconstruction is important, because in the normal ventricle, the apex is functional and creates a vortex that helps cardiac muscle work. The new apex that is created during the ventricular reconstruction should prevent the ventricle from becoming spherical (again), a situation that may lead to creation of (or worsening of existing) mitral regurgitation. However, current approaches do not adequately provide for reconstruction of the apex of the heart. For example, failure to balance the position of the apex and volume has potentially deleterious impact on patient safety. A suboptimal short axis/long axis ratio, (i.e., apex improperly reconstructed too close to the mitral plane), may contribute to the development of late mitral regurgitation, even in cases where pre-existing mitral function is normal. The objective in optimizing the locus of the apex of the left ventricle should combine the optimal reduction of both the short axis with proper identification of the position of the new apex.

The position of the apex is important for normal functioning of the mitral valve. Ischemic functional mitral regurgitation is more frequent in dilated ventricles. In an enlarged heart, papillary muscles are displaced toward the lateral wall, losing their normal orientation toward the apex and increasing the distance between them. In this condition the posterior leaflet of the valve is retracted, the posterior annulus is dilated, and the valve becomes incompetent. Therefore this invention has the additional benefit of supporting proper mitral function.

It should therefore be understood that a device which can assist the surgeon to locate and anatomically configure the apex will provide a significant advantage to the surgeon and the patient. The invention disclosed here will cover the creation of new apex of a heart. In so doing, it will also direct the surgeon to proper size determination.

SUMMARY

A method and system for use in resizing the left ventricle of the heart of a patient from a diseased state to an appropriate resized state is disclosed. The method includes the steps of determining the body surface area of the patient; determining a characteristic of the left ventricle which is the same in the diseased state as in the resized state; determining an appropriate sizer based on the determined body surface area of the patient and the characteristic of the left ventricle which is the same in the diseased state as in the resized state; identifying akinetic tissue within a heart chamber wall; making an incision through the akinetic tissue in the chamber wall; inserting said appropriate sizer into the chamber through the incision; removing the sizer; and, closing the incision.

BRIEF DESCRIPTION OF THE DRAWINGS

FIG. 7 is a back view of the preferred embodiment of the present sizer.

FIG. 10 is a view of a human heart with a portion cut away to expose the interior of the left ventricle.

FIG. 10A is a cross sectional view of a human heart.

FIG. 11A is a view of a diseased human heart with a portion cut away to expose the interior and to show a sizer installed in the left ventricle.

FIG. 11B is a view of an appropriately resized human heart with a portion cut away to expose the interior and to show a sizer installed in the left ventricle.

FIG. 16 is an isometric view of an alternative embodiment of the sizer of the present invention.

FIG. 17 is a block diagram schematically illustrating one embodiment of the process of the present invention.

FIG. 18 is a block diagram schematically illustrating another embodiment of the process of the presenter invention.

DETAILED DESCRIPTION OF THE PREFERRED EMBODIMENT

Brief Summary of a Preferred Method

Figure 1:
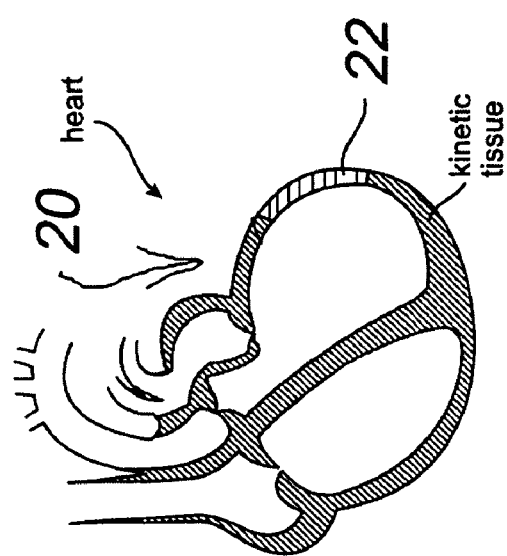
FIG. 1 is a cross sectional view illustrating a weakened heart chamber before reconstruction.
Figure 2:
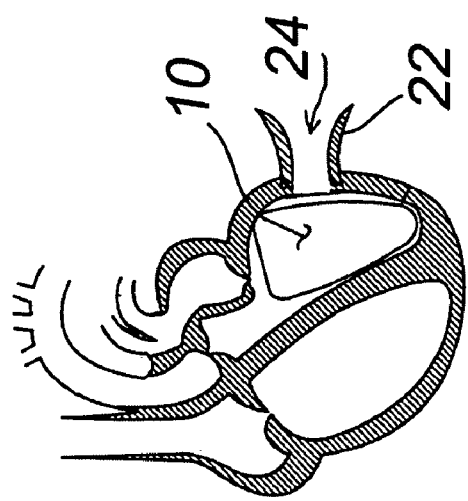
FIG. 2 is a cross sectional view of a heart chamber illustrating one embodiment of this invention as employed in a procedure to reconstruct a heart chamber.
Figure 3:
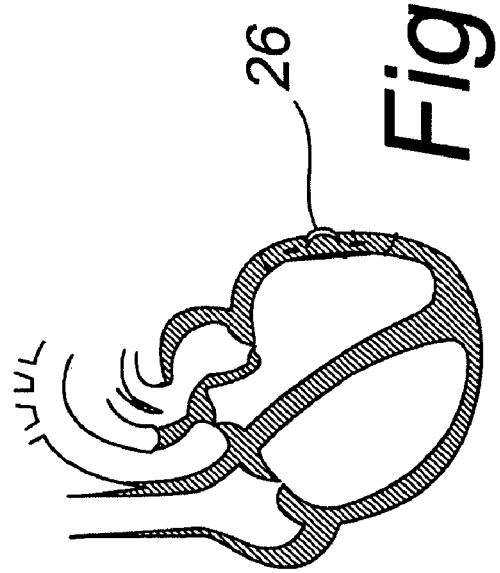
FIG. 3 is a cross sectional view illustrating a heart chamber after reconstruction.

FIGS. 1-3 schematically illustrate a method for reconstructing a left ventricle using a sizing device 10. Referring to FIG. 1, before reconstruction, the heart chamber, in this case the left ventricle 20, is abnormally dilated. A portion of the ventricle wall 22 has become nonfunctioning, damaged, akinetic or dyskinetic. For simplicity such tissue will be referred to hereinafter as nonfunctioning or akinetic. The surgeon makes an incision 24 within the akinetic tissue 22 and folds back the akinetic tissue 22. Referring to FIGS. 2 and 3, the sizing device 10 is then inserted into the ventricle 20 through the incision. Using a suture 26, the surgeon weaves a purse-string stitch to exclude the akinetic tissue 22 and to bring the ventricle wall against the sizing device 10, using the sizing device 10 as a form or template to gauge the correct or appropriate size of the reformed left ventricle. Then the surgeon removes the sizing device 10 and closes the incision 24. For simplicity the device 10 will be called a sizer or sizing device although it should be understood that the device is used by the surgeon to resize the left ventricle.

Figure 4:
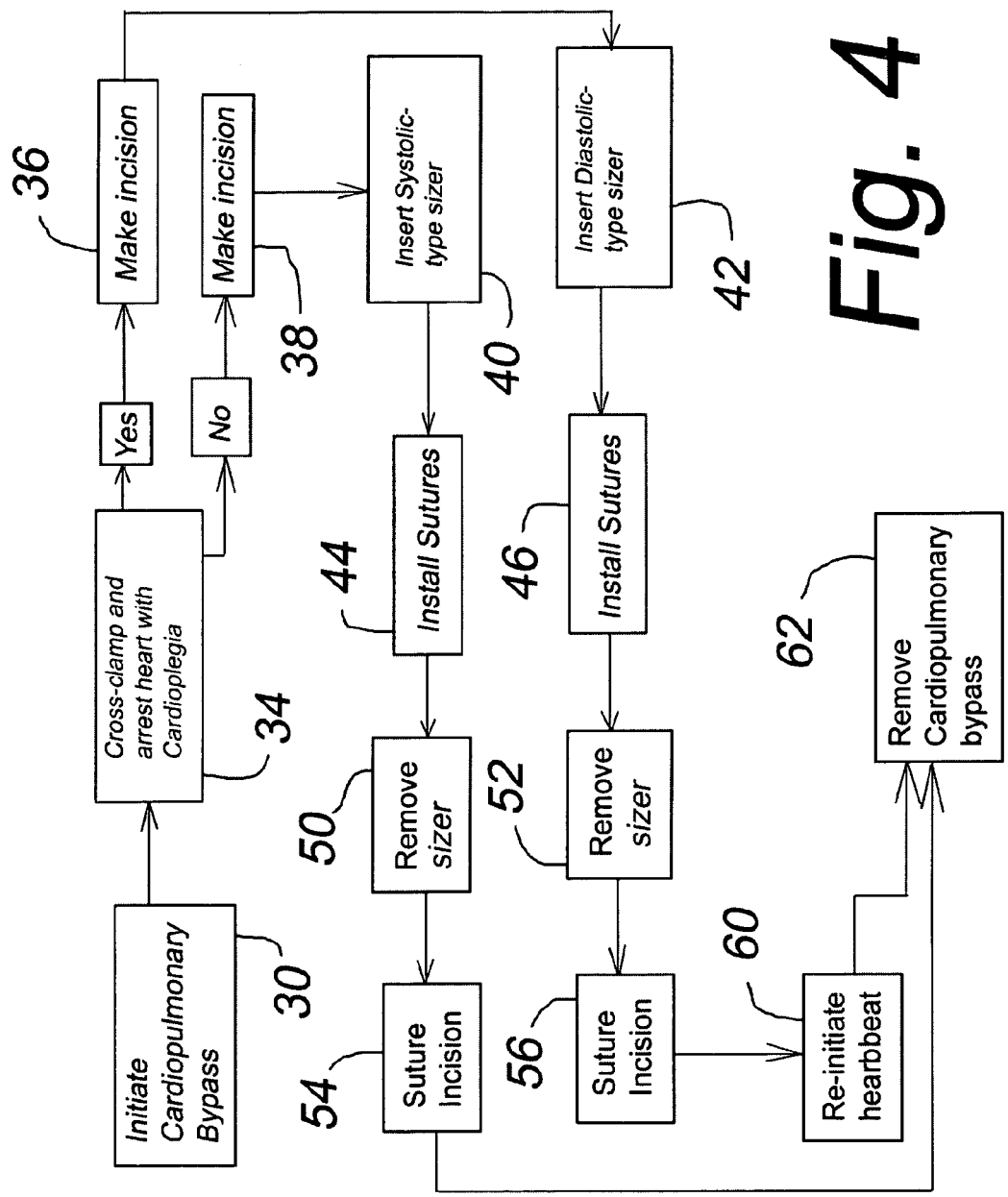
FIG. 4 is a block diagram schematically illustrating an overview of the process of this invention.
Figure 6:
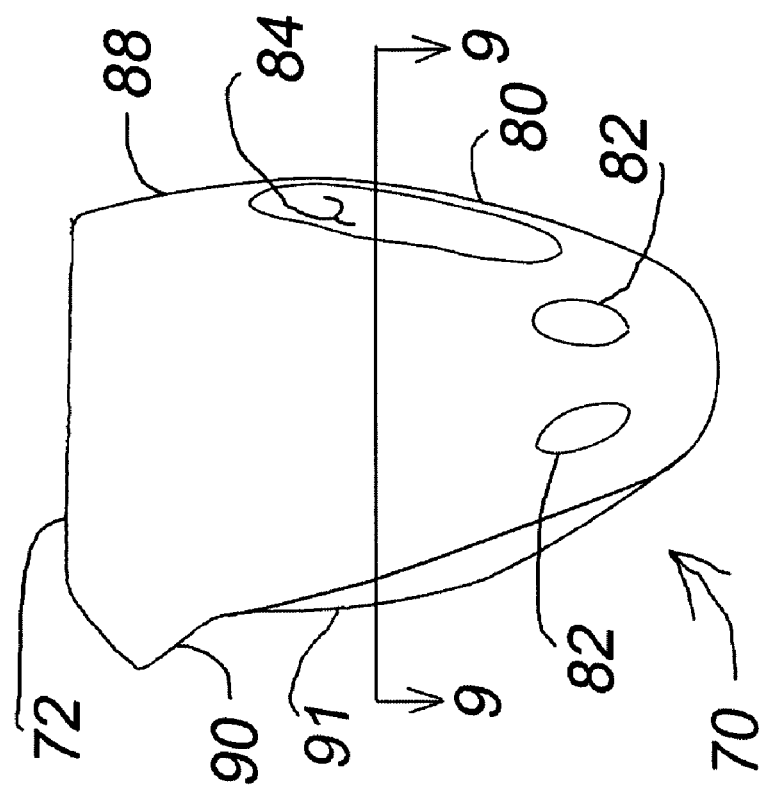
FIG. 6 is a left side view of the preferred embodiment of the present sizer.
Figure 5:
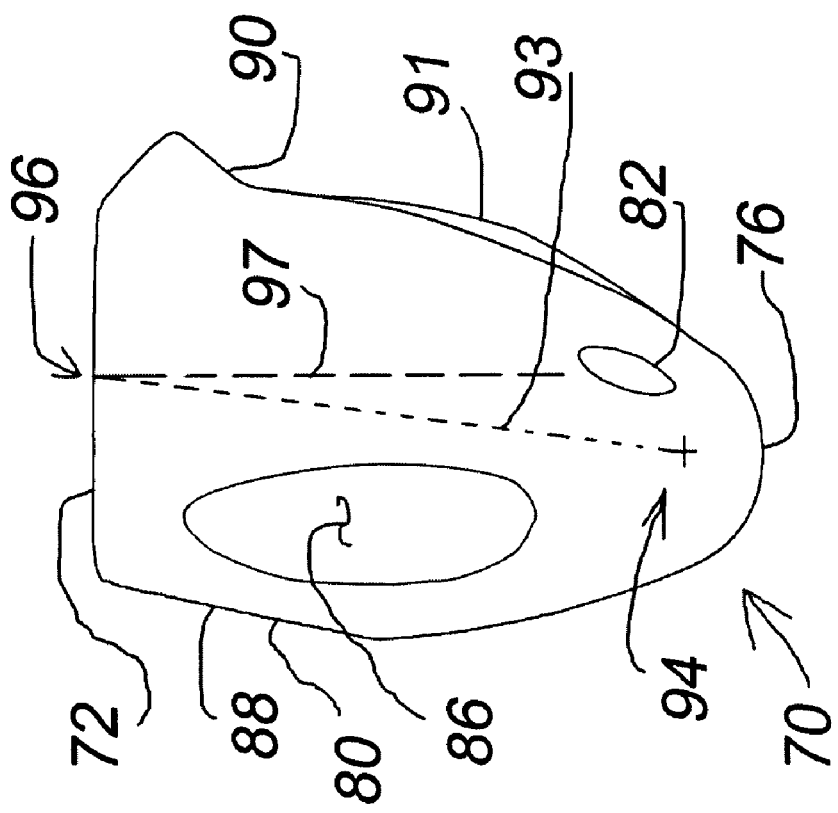
FIG. 5 is a right side view of the preferred embodiment of the present sizer.
Figure 8:
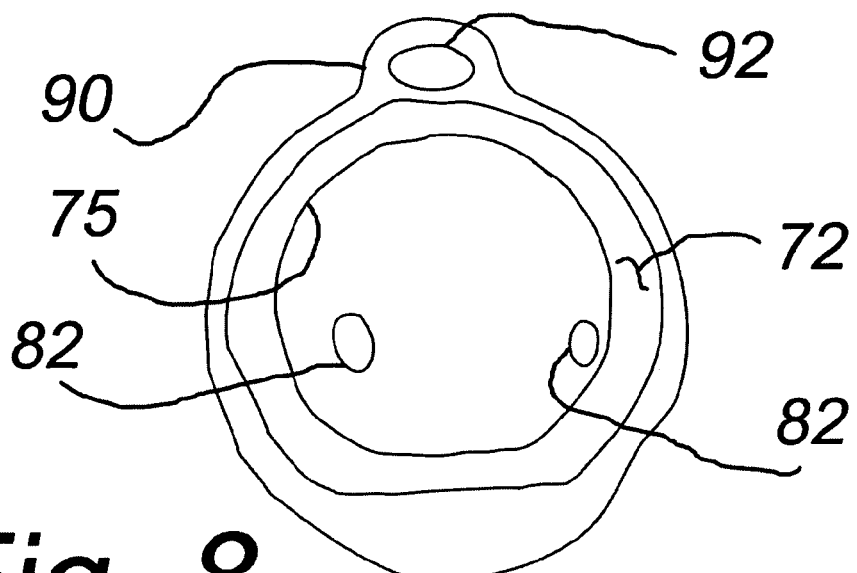
FIG. 8 is a top view of the preferred embodiment of the present sizer.
Figure 9:
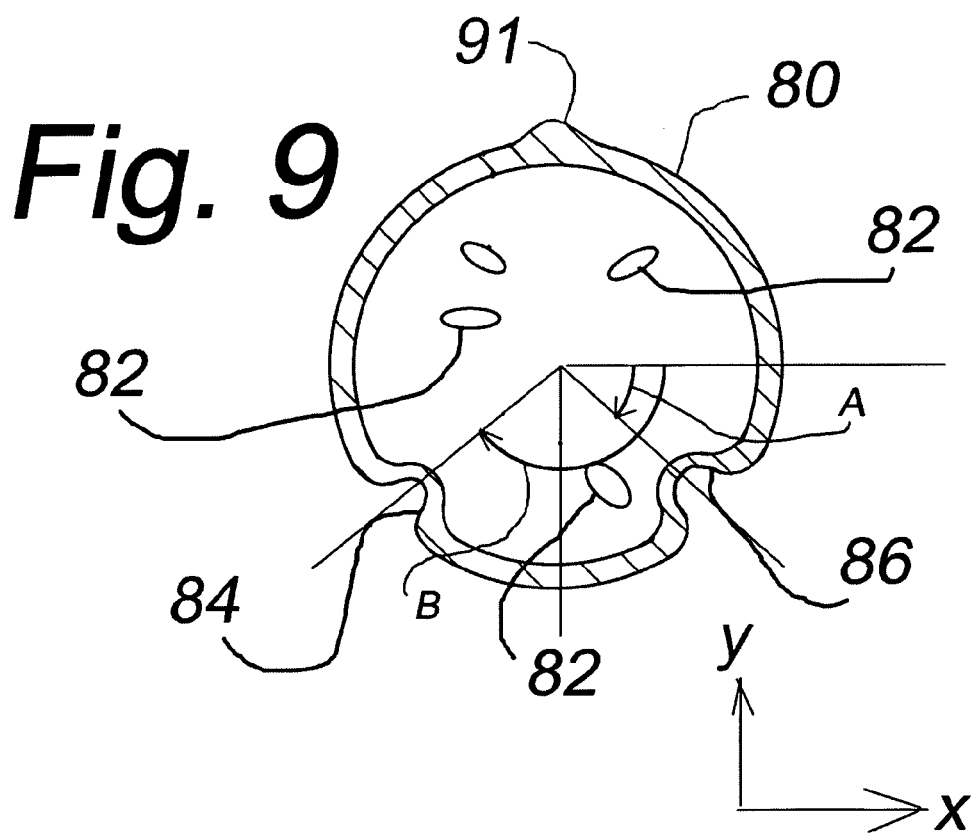
FIG. 9 is a section view of the preferred embodiment of the present sizer taken along line 9-9 in FIG. 6.

With reference to FIG. 4, during the process described above, a conventional cardiopulmonary bypass system is used to the oxygenate patient's blood, according to Step 30. Also, preferably the patient's heart continues to beat, although in some cases it may be advantageous to arrest the beating of the heart using conventional cross clamping and cardioplegic procedures, step 34. In either case the surgeon then makes an incision in the akinetic portion of the heart, according to step 36 or 38. If the heart has been stopped, the surgeon then installs a sizer which has been specifically designed to be used with an arrested heart, which can be called a diastolic-type sizer, step 40, whereas if the heart continues to beat the surgeon installs a sizer which has been specifically designed to be used with a beating heart, which can be called a systolic-type sizer, step 42. The two types of sizers will be discussed below.

Thereafter the surgeon installs sutures, steps 44 and 46, reforms the heart, removes the sizer, steps 50 and 52, and sutures the incision, steps 54 and 56. If the heartbeat had been stopped, it is then reinitiated, step 60, and then the cardiopulmonary bypass system is removed, step 62.

Sizing Device

Referring to FIGS. 1-3, the sizing device 10 is used as a guide or template to guide surgical or alternative reconstruction to what has been predetermined to be a more optimum size of the left ventricle. In this application, the sizing device 10 may act as an idealized anatomical sizer and helps the surgeon to know how much of the ventricle 20 to bring together for a more optimum size, without the risk of making the resulting ventricle too small.

The sizing device 10 can help to improve the resulting size f the heart according to the requirements of a particular patient. A detailed pre-reconstruction analysis based on characteristics of the dysfunctional structure and those of the normal/optimal state may be conducted to aid in choosing the appropriate size for the sizing device 10. Thus, the use of the sizing device 10 as a guide can help to eliminate the mistakes that occur when a practitioner relies only on his judgment to estimate the appropriate size.

The sizing device 10 may be utilized during an open field or minimally invasive surgical procedure. It may also be deployed through a standard or modified endoscope. The sizing device 10 may also be used for laparoscopic, robotically assisted and/or percutaneous procedures. The sizing device 10 is compressible and re-expandable to allow compression during insertion and withdrawal, and re-expansion once inserted into the organ. The ability to compress the sizing device 10 into a reduced cross section profile facilitates insertion and removal.

The sizing device 10 may have a stock size or it may be made custom for a particular patient's anatomy. For example, the device may be available in multiple stock sizes according to volume (e.g. 90, 110 and 130 cc or small, medium, and large). If it is custom made for a particular patient, MRI, PET scan, Echo, ultrasound, any other visualization techniques, or any other appropriate method may be used to determine the pre-condition and/or optimum post-procedure size of the ventricle, as described in more detail in the following provisional patent applications incorporated herein in their entirety by reference: U.S. Provisional Patent Application Ser. No. 60/466,653, filed on Apr. 29, 2003 and titled Ventricular Restoration; U.S. Provisional Patent Application Ser. No. 60/499,946, filed on Sep. 2, 2003 and titled System and Method of Use to Employ Imaging Technology for Diagnosis, Measurement, Standardization, and Follow-up of Disease Processes and Determine Optimal Treatment; and U.S. Provisional Patent Application Ser. No. 60/518,270, filed Nov. 5, 2003 and titled Methods and Devices for Tracking Acute Myocardial Infarction.

It should be recognized that the sizer 10 is schematically illustrated in FIG. 2, and the exact configuration of the sizer 10 can be various geometries as explained below. Referring to FIGS. 5-9 a preferred embodiment of a sizer is shown. The sizer 70 illustrated in FIGS. 5-9 is formed of resilient plastic material and is hollow in order to be easily deformable. The sizer 10 is formed of a compliant material that is resistant to permanent deformation so that the sizer 10 can be compressed to be inserted into the heart and once inside to return to its original size. The sizer 70 has a flat, annular top surface 72 and an arcuate portion 74 shaped similar to an egg. The annular top surface 72 includes a circular hole 75 which communicates with the hollow interior of the sizer 70. The arcuate portion 74 comprises a rounded apex 76 connected to the top surface 72 by a roughly cylindrical portion 80. Four holes 82 are formed in the sizer 70 near the apex 76, and two indentations 84 and 86 are formed in the cylindrical portion 80. As an example, for a sizer 70 having a volume of 100 cc, the length of the sizer 70 measured from the annular top surface 72 to the tip of the apex 76 is about 73 mm. For the same 100 cc sizer, measured from the top surface 72, the first indentation 84 begins at about 7 mm and ends at about 45 mm, while the second indentation 86 begins at about 18 mm and ends at about 55 mm. Also, measured according to the coordinate system shown in FIG. 9 and relative to the center 87 of the cylindrical portion 80, the center line of indentation 86 is located at an angle A of about 40 degrees, and the centerline of indentation 84 is located at and angle B of about 125 degrees. A flat section 88 is formed in the cylindrical portion 80 near the top surface 72, and a protrusion 90 is also formed near the top surface 72. A circular hole 92 is formed in the protrusion 90, and a ridge 91 extends along the side of the sizer 70 beginning at the protrusion 90. It should be noted that the sizer 70 is asymmetrical in certain respects. For example, the rounded apex 76 is a section of a sphere. If one were to draw a line 93 connecting the center (labeled 94) of that section with the center (labeled 96) of circular hole 75, the line would deviate from a line 97 beginning at the center of the circular hole 75 and drawn perpendicular to the annular top surface 72. Specifically, if one considers the coordinate system shown in FIG. 5, line 93 deviates from line 97 by and angle C of about 5 degrees in the x-y plane, although line 93 does not deviate from line 97 in the y-z plane.

Figure 11:
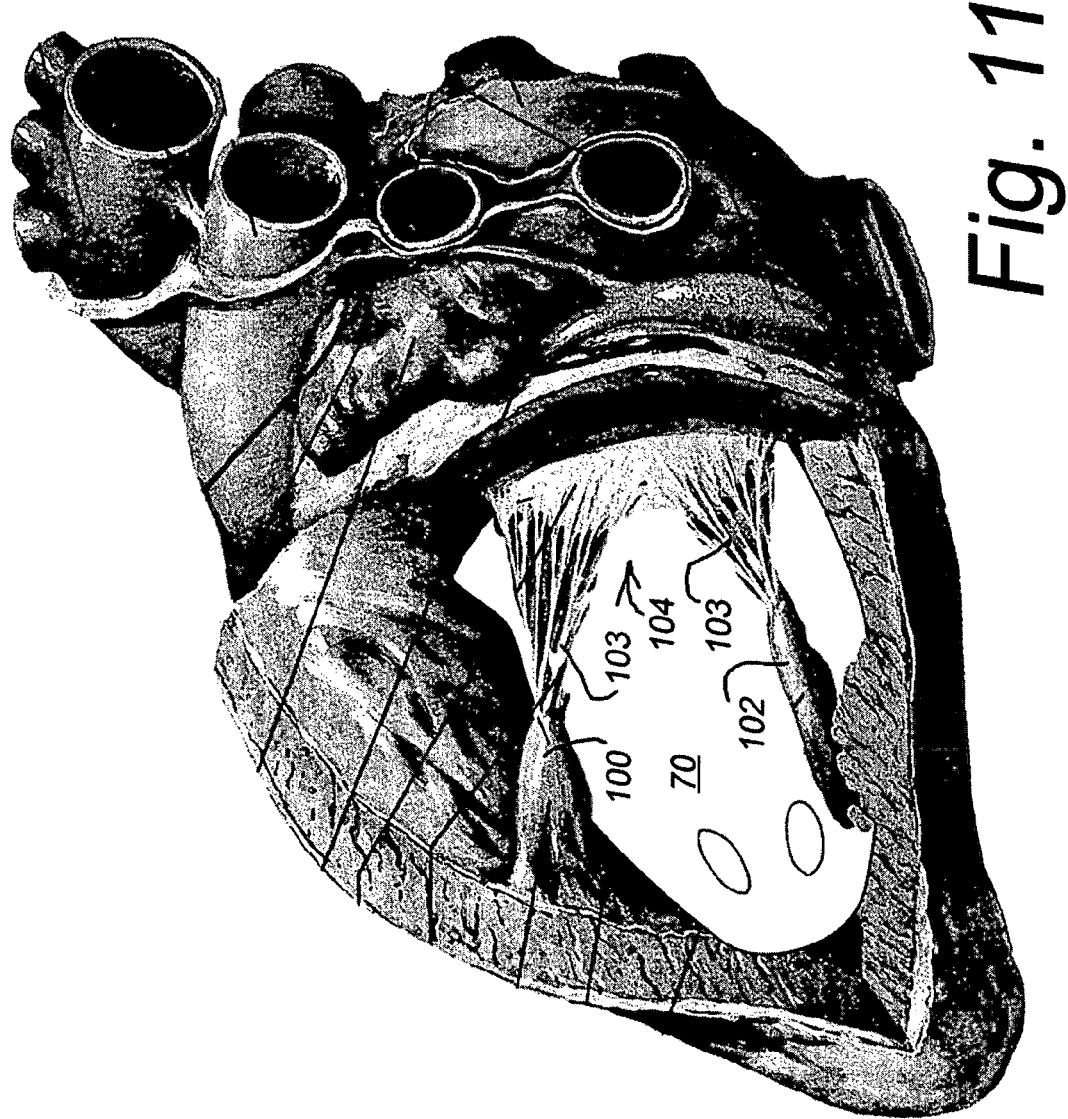
FIG. 11 is a view of a human heart with a portion cut away to expose the interior and to show a sizer installed in the left ventricle.

Tuning now to FIGS. 10 and 11, an illustration of a heart is provided showing the interior of the left ventricle. In these illustrations the heart has been cut and a portion folded back to expose the interior and show the placement of the sizer 70. The anterior papillary muscle 100 and the posterior papillary muscle 102 are shown and each of the muscles is connected to chordae tendinae 103 which in turn are connected to the mitral valve 104. FIG. 10A shows the heart cut open to show the left and right ventricles. Turning to FIG. 11, the sizer 70 is shown as located in the left ventricle. It should be understood that the indentations 84 and 86 of the sizer 70 are shaped and located so as to rest against the anterior papillary muscle 100 and the posterior papillary muscle 102, respectively, and their corresponding chordae tendinae 103. In other words, the indentations 84 and 86 provide space for the muscles and chordae tendinae so those portions of the heart are not subject to excessive pressure from the sizer 70. Similarly, the circular hole 72 allows the mitral valve 104 to open and close with minimal restriction, and the hole 92 accommodates aortic outflow.

The flat portion 88 protects the chordae from excessive pressure by the sizer 70, the indentations 84 and 86, the protrusion 90, the annular top surface 72 and the ridge 91 permit the surgeon to properly align the sizer 70 in the left ventricle to permit correct location of the apex of the left ventricle when the ventricle is resized by the surgeon. When the sizer 70 is correctly located in the left ventricle as shown in FIG. 11, the annular top surface 72 contacts the base of the left ventricle, and the sizer 70 is aligned so that the indentations align with the papillary muscles 100 and 102 and the circular hole aligns with the aortic valve (not shown). Furthermore, the ridge 91 is located abutting the septum 105. When such alignment is achieved, the rounded apex 76 of the sizer is optimally located with respect to where the apex of the left ventricle should be in the appropriate or correct reconstructed left ventricle. Moreover, when the left ventricle is reconstructed adjacent the sizer, the apex of the left ventricle and the sides of the left ventricle are properly formed and located as they would be in a healthy heart. For this reason the sizer 70 can be considered to be an "apex locator."

Turning now to FIGS. 11A and 11B, the operation of the sizer as an apex locator is schematically illustrated. In FIG. 11A a pre-operative heart is shown in which the akinetic portion 22 encompasses the location of the ventricle apex 113. As can be seen, diseased apex 113 has been physically remodeled differently from a normal apex, and the interior of the ventricle in the area of the diseased apex 113 does not conform to the sizer 70. After resizing, the ventricle is as illustrated in FIG. 11B, and the ventricle apex 116 is located adjacent the apex 76 of the shaper 70. It should be understood that when the annular top surface 72 abuts the base 115 of the heart and the shaper is properly oriented as discussed above, the apex 76 of the shaper is properly positioned so that when the heart is reformed to conform to the shaper, the reformed ventricle apex 116 is correctly located as it would be in a healthy heart. To illustrate this a line 116a is drawn coincident with the base 115, and a line 116b is drawn perpendicular to the line 116a from the center of the base 115. Also, a line 117 is drawn from the center of the base 115 to the reformed apex 116. It can be seen that the line 117 deviates from line 116b, and the angle of deviation C can be in the range of about 0 to 15 degrees and normally is about 5 degrees. In a healthy heart the apex is located at about the same angle.

Referring to FIGS. 12-16, alternative sizes of the sizer 10 are illustrated. The sizing device 10 may be tulip geometry or egg geometry, and the sizing device 10 may comprise a parabolic geometry or other suitable geometries. In some embodiments the sizing device 10 may be symmetric or asymmetric, anywhere on the device, top, bottom and/or body. In some embodiments top edge 111 of the sizing device 10 maybe straight and flat, sinusoidal, a combination of these geometries, or made into another suitable geometry.

In one embodiment, the sizing device 10 may have one or more reference marks. The reference marks may comprise a single mark, multiple marks, a grid, or any other appropriate markings. The reference marks may be used for orienting or positioning the sizing device 10 within the left ventricle, for guiding the suture line, for guiding the positioning of tissue, and/or for any other suitable purpose. These reference marks may be molded onto the sizing device 10 as indentations or raised areas. Alternately, the reference marks may be printed on or otherwise applied to the sizing device 10.

Figure 12:
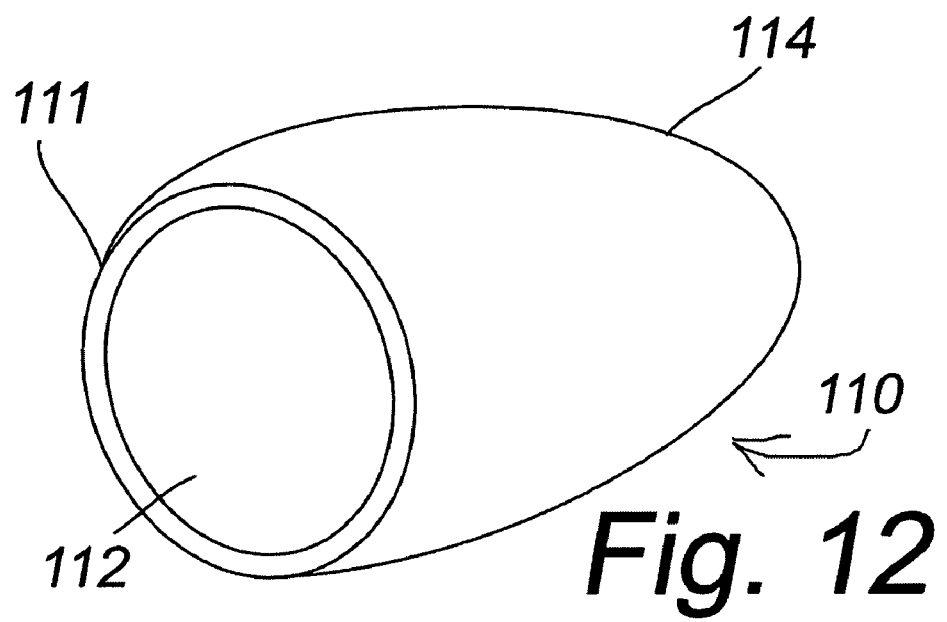
FIG. 12 is an isometric view of an alternative embodiment of the sizer of the present invention.

As shown in FIG. 12, in one embodiment the sizing device 110 may be hollow such that it partially or entirely encloses an interior space 112. In this embodiment, one or both ends of the sizing device 110 may be either covered, partially covered, or open. That can aid in preventing inadvertent expansion of the sizing device 110. In another embodiment, the sizing device 110 may have one or more cutouts and/or indentations so as not to damage structures such as papillary muscles, chordae tendinae, valves or valve structures including the annulus.

The outside 114 of the sizing device 110 maybe smooth, textured, or a combination of both smooth and textured. In one embodiment, a lubricant, such as parylene, may be applied to the exterior and or interior of the sizing device 110. Additionally, the sizing device 110 may comprise holes, slots, or thin or weakened wall areas to initiate or focus the bending or folding during insertion and removal and to assist with insertion and removal. In another embodiment, the sizing device 110 may comprise "pods" on the surface connected to an airtight lumen or lumens that, when connected to suction, can enhance fixation or stabilization.

Figure 13:
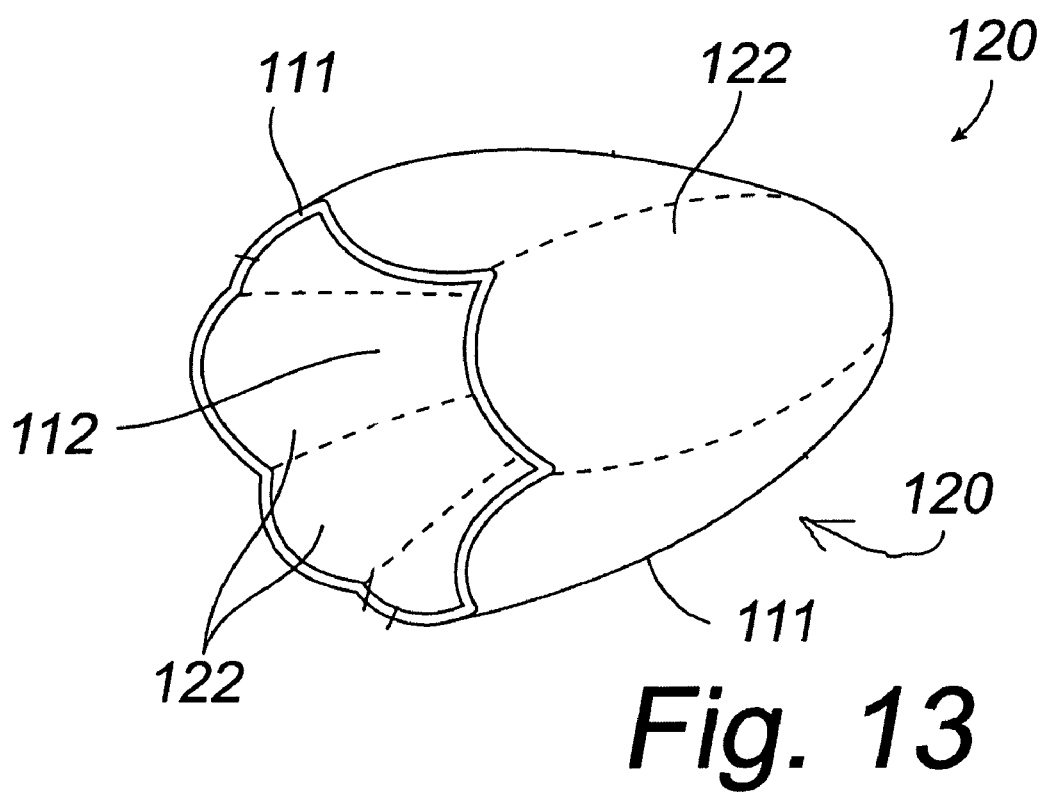
FIG. 13 is an isometric view of an alternative embodiment of the sizer of the present invention.

Referring to FIG. 13, in another embodiment the sizing device 120 may have one or more removable sections 122. A perforated or weakened area 124 can facilitate and/or guide the removal of one or more sections 122. By removing the one or more sections 122, a practitioner can adjust the size of the sizing device 120.

Figure 14:
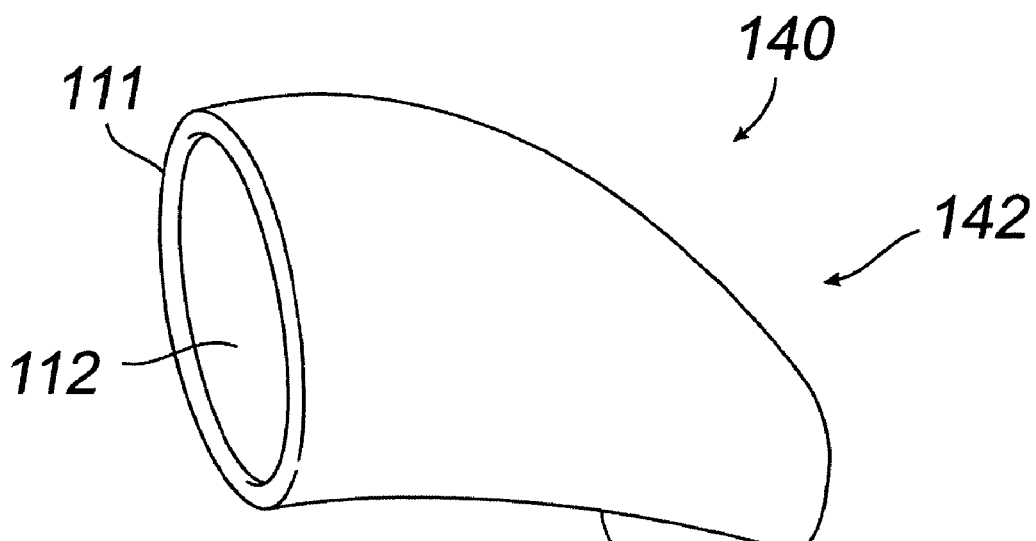
FIG. 14 is an isometric view of an alternative embodiment of the sizer of the present invention.

In the embodiment shown in FIG. 14, the sizing device 140 is asymmetrical toward its distal end 142. The asymmetrical configuration may allow the sizing device 140 to better accommodate surrounding anatomical structures when in the correct position and orientation. It may also act as a guide to aid the practitioner in positioning and orienting the sizing device 140 within the heart chamber.

One embodiment of the compressible sizing device 10 may be covered with an airtight material and connected to a lumen for loading and deployment. A Luer, stopcock or another type of connector can be placed on the opposite end of the lumen from the device so that when a vacuum is created (by using a syringe or the vacuum supplied in the surgical suite, or any other appropriate source), the sponge or foam will collapse down to a reduced cross-sectional profile for insertion and removal from the ventricle (or other location). Once the vacuum has been removed, the sponge or foam sizing device 10 self expands to its natural size.

Because in this embodiment the sizing device 10 need not include a bladder or balloon component on the surface, it is less likely to be functionally impaired by suture, blade, or any other sharp instrument. However, in an alternate embodiment, the sizing device 10 may have an internal bladder that can be aspirated. A Luer-lock fitting with a syringe can be used for aspirating the bladder to control its size.

Figure 15:
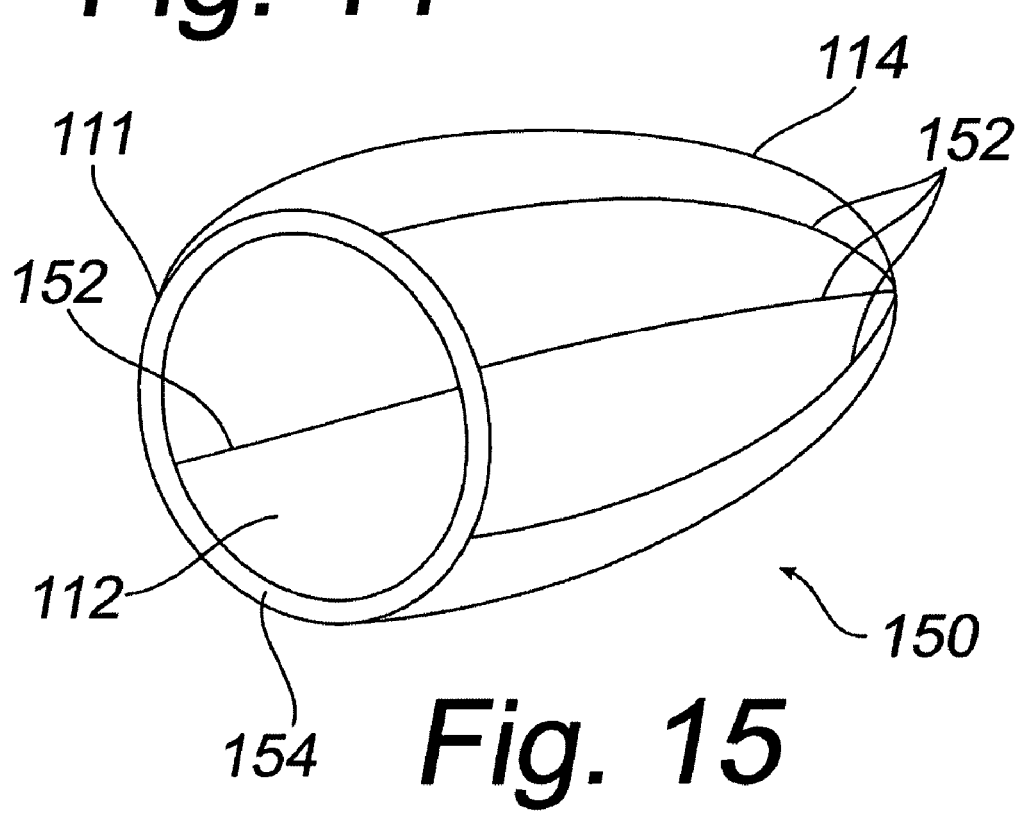
FIG. 15 is an isometric view of an alternative embodiment of the sizer of the present invention.

As shown in FIG. 15, the sizing device 150 may also include one or more reinforcing elements 152 to provide additional support. The reinforcing elements 152 may include one or more strips, sheets, wires, rods, tubes, mandrels, any combination of these. The reinforcing member or members 152 may be located on the inside surface of the walls 154 of the sizing device 150, on the outside of the walls 154, within the walls 154, or any combination of these locations. The inclusion of these components may assist with self-expansion of the device.

One method of constructing the sizing device 10 is through molding. Alternative construction methods may include stereo lithography, casting, sintering, weaving, extrusion, a dip coating process, spraying, laminating, a combination of any of these, or another suitable method or process.

In one embodiment, the sizing device 10 may comprise a superelastic or shape memory material, a material that is inherently resistant to permanent deformation or is processed to be resistant to permanent deformation. One such shape memory material is the superelastic metal alloy nitinol, but many other materials may be used including other superelastic metal alloys, or superelastic shape-memory polymers. The shape memory material may permit fabrication of a sizing device 10 that is collapsible to a smaller size for insertion and self-expands once released in the organ. Once the compressed device is no longer constrained, it can snap back into its fully expanded geometry. The expansion of the sizing device 10 may be achieved by the inherent spring of the material as in a superelastic material. In other embodiments the expansion of the sizing device 10 may be achieved by raising the ambient or component temperature (direct heating or the body's heat) for a shape memory effect.

The sizing device 10 may comprise heterogeneous materials. For example, some portions may be softer and-more compressible while others may be stiffer and smoother. That can help to reduce trauma during placement and removal.

In one embodiment, the sizing device 10 comprises polyurethane or polyethylene, but other suitable materials may be used. In other embodiments the sizing device 10 may comprise any of the following: a metal, a metal alloy, a polymer, rubber, foam, a sponge, silicone, (including silicone polyether and silicone polycarbonate, etc.), ePTFE, Dacron®, a combination of these materials, or any of these materials combined with any other suitable material. The device may be partially or totally radio-opaque by adding material such as barium sulfate or bismuth tri-oxide or another suitable material. In other embodiments, any portion of the sizing device 10 may be partially or completely coated with a biocompatible material, such as parylene, expanded polytetrafluoroethylene (ePTFE), polyester, polyurethane, silicone, Dacron®, urethane, and/or a composite or combination of these or of another suitable material or materials.

The sizing device 10 may comprise a material that is either substantially translucent, substantially opaque, or a combination of both at various locations. In one embodiment, the sizing device 10 may comprise a material having a color that contrasts with the natural color of cardiac tissue. The contrasting color can help a practitioner to more easily visually distinguish between the sizing device 10 and the cardiac tissue.

In alternate embodiments, the sizing device 10 may include the use of a vacuum, protrusions, knurling, surface dimples or spheres, compliant coatings, raised bands and/or lines, horizontal rings or other designs and methods to assist with temporarily holding the device against tissue to prevent slippage while in use. The vacuum utility may be accomplished using lumens or tubes with ports that allow the suction to contact tissue. The lumens or tubes may be connected to a vacuum source at the proximal end of the device (which may be on or near a handle), using at least one Luer or similar type of connector. The vacuum lumens or tubes may be independent or connected to a single proximal connector.

The sizing device 10 may also comprise a "leash" or "tether" element used to assist in retrieval from the ventricular cavity. The leash element may be made from a single- or multi-element string. The string may or may not be braided. Alternatively, the leash element may be made from any other suitable component and material. The leash element may be attached to the sizing device 10 during fabrication, or as a second process. This element may be attached internally such that when tension is applied, the remote site of attachment may invaginate and deform the sizing device 10 in a way that is advantageous for placement, removal, or other function. The leash may be connected at one or more locations, anywhere on or in the sizing device 10. The leash may be a stiff or partially flexible structure, or a combination of both.

In another embodiment, the sizing device 10 may comprise one or more holes that permit a practitioner to attach suture material or another suitable material to the sizing device to form a leash. Other embodiments may include more than one leash or handle to manipulate, stabilize, remove or otherwise employ the sizing device 10 in its intended function. The end of the leash may include a pull tab located on the leash end opposite from the sizing device 10.

Referring to FIG. 16, in one embodiment the sizing device 160 may comprise one or more holes 162 to affect flexibility or other physical properties. In other embodiments, the sizing device 160 may comprise one or more slots or other piercings instead of, or in addition to, the one or more holes. Additionally at least one hole 162 may be used for and may enable venting, suction, and drainage during the procedure, something not possible when utilizing a balloon type sizing or shaping device. This process, known as the Smith-Luver Technique, is an important advantage in minimally invasive surgical ventricular reconstruction procedures.

Determining the Correct Volume of the Sizer

As discussed above, it is important that the sizer be the correct volume to assist the surgeon in reforming the left ventricle to the correct or appropriate size. It should be understood that in the present context the "volume" of the sizer is the volume enclosed by the external surface of the sizer, assuming that the circular hole 75 is closed. In other words, the "volume" of the sizer can be thought of as the volume of the ventricle enclosing the sizer. With reference to FIG. 17, according to one embodiment of the present method to determine the correct volume of the sizer, the method includes 1) determining the patient's body surface area, step 160; 2) determining the short axis left ventricle diameter at papillary muscle tips before surgery, step 162; and 3) determining the appropriate volume of the sizer based on the patient's body surface area and the short axis left ventricle diameter at papillary muscle tips before surgery, step 164.

To determine the patient's body surface area various conventional procedures may be used. For example, one can measure the patient's body weight and body height and then estimate the body surface area according to the following formula developed by DuBois and DuBois:

$$BSA = 0.0001 * 71.84(w^{0.425})(h^{0.725})$$

Where:
BSA=body surface area in square meters
W=weight in kilograms
H=height in centimeters To determine the short axis left ventricle diameter at papillary muscle tips before surgery conventional methods can be used, such as cardiac catheterization, cardiac MRI, or echocardiography. Once these parameters have been determined the correct volume of the sizer is determined as follows.

$V_1$=BSA * 55 (rounded to the nearest 10)
d=Measured diameter at papillary muscle tips in centimeters
$V_2$ is determined using the following table, according to the preferred embodiment.

| Measured diameter at papillary muscle (d) tips in centimeters | Volume of Sizer in cubic centimeters (or cc) |
|---|---|
| 4.5-4.87 | 90 |
| 4.88-5.02 | 100 |
| 5.03-5.17 | 110 |
| 5.18-5.32 | 120 |
| 5.33-5.47 | 130 |
| 5.48-6.00 | 140 |

Alternatively, $V_2$ can be determined according to the following equation $$V_2 = d * X$$

Where X ranges from about 18.5 to about 25.5 square centimeters. More specifically, if d is in the range of about 4.88-5.02 then X=19.9-20.5.

Once $V_1$ and $V_2$ have been determined, the correct volume for the sizer is selected as the smaller of $V_1$ and $V_2$. The reason for selecting the smaller volume should be understood to be based on the fact that sizers are normally made in a limited number of discrete sizes, e.g. 90, 110, 110 and 120 cubic centimeters. Thus a surgeon has available one of these various sizes and must select the one which will provide the best fit for the patient and not result in a reformed left ventricle which is too large. Rather, we have found that it is preferable that a reformed left ventricle be small instead of being too large. Furthermore, using as an example the sizer configured according to FIGS. 5-9, in order to properly fit that patient, the diameter of the cylindrical portion 80 must be matched to the short axis left ventricle diameter at papillary muscle tips of the patient's left ventricle. Also, it should be understood that we determined empirically by measuring the diameters of sizers having the design shown in FIGS. 5-9. If a sizer having a different configuration were used, then the value of X would be different and the table relating measured diameter at papillary muscle tips in centimeters to volume of sizer in cubic centimeters could be different.

It should be understood that the short axis left ventricle diameter at papillary muscle tips before surgery is a characteristic of the left ventricle which is not altered by the reformation of the left ventricle. Instead of the short axis left ventricle diameter at papillary muscle tips before surgery, alternative parameters of the heart which are not altered by the reformation of the left ventricle could be used. Thus, according to an alternative embodiment of a method to determine the correct volume of the sizer, and with reference to FIG. 18, an alternative embodiment of the method includes 1) determining the patient's body surface area, step 170; 2) determining the size of a characteristic of the left ventricle which is not altered by the reformation of the left ventricle, step 172; and 3) determining the appropriate volume of the sizer based on the patient's body surface area and the size of the characteristic of the left ventricle which is not altered by the reformation of the left ventricle, step 174.

Figure 19:
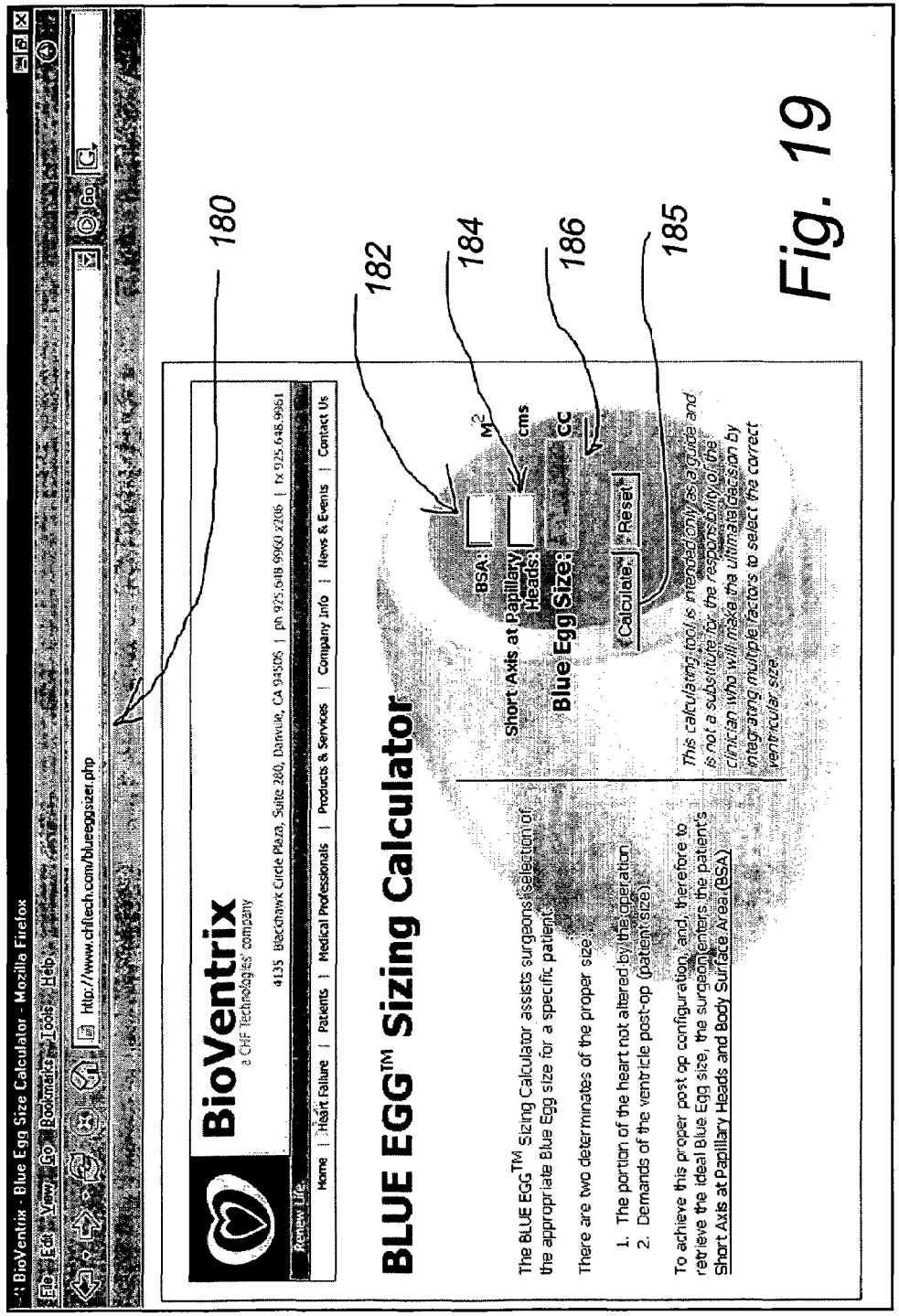
FIG. 19 is a view of a computer monitor illustrating one embodiment of the process of the present invention.

Turning now to FIG. 19, the present method is illustrated as implemented in an Internet-based system. FIG. 19 illustrates a user's computer monitor. It should be understood that the method shown in FIG. 17 or 18 is implemented on a computer system or server maintained by the manager of the system, in this case "Bioventrix". A user such as a surgeon who wishes to determine the appropriate sizer to use enters the URL of the appropriate file located on the server maintained by Bioventrix, namely, http://www.bioventrix.com/blueeggsizer.php, in the user's web browser in field 180, and the screen as shown in FIG. 19 is then displayed on the user's computer monitor. The user then enters the patient's body surface area in field 182 and the short axis at papillary heads in field 184 and clicks on the button 185 labeled "calculate". The server computer then utilizes the method shown in FIG. 17 or 18 to calculate the size of the appropriate sizer, which in this example is called a "Blue Egg" sizing device, and displays the size in field 186. It should be understood that the server computer is programmed to accept data entered in fields 180 and 182 only within predetermined ranges. This helps ensure that the data entered by the user is accurate.

There are a number of alternative embodiments to the preferred embodiment described above. For example, the server computer may contain a function where the inputs are redisplayed for the user, and the user will be required to confirm the inputs before the result is displayed. The purpose of this function is to minimize potential errors.

The program can exist in the form of an electronic file, which can be downloaded to remote sites or available on the Internet.

The server program can contain firewalls, encryption, security, password access, or other appropriate mechanisms to ensure both proprietary and safety considerations.

In another alternative embodiment, there may be a diagram or picture in some form of the sized element in its intended use. For example, there may be a diagram of a heart with a dilated Left Ventricle, and the degree of dilation may change with the data input. There may be a Blue Egg portrayal superimposed on the LV image so that the relative size of the Blue Egg selected by the device may be visualized by the user.

In another alternative embodiment, the software program may also contain such elements as tutorials, diagrams, links to other web sites containing related or unrelated information. Also, the program may ask the user for other input, such as information about the patient not required for size determination As another alternative, instead of a computer program, a "hard copy" chart of the data could be provided. Alternatively, the method could exist in an electronic form, such as a disk, tape, downloaded file, and be in the possession of the user. In this embodiment, the file may be read on a hand held (PDA) device, personal computer (PC), Local Network (e.g., hospital or business).

Systolic-Type Sizers

Many surgeons are convinced there is a benefit to reconstructing the left ventricle while the heart is beating. This technique is deemed advantageous by its proponents because it allows assessment of the so called "border zone" where cardiac wall-thickening identifies the appropriate margin of the endocardium for the accomplishment of the repair. While the boundary between the more functional and less functional portions of the wall may be established when the left ventricle is reconstructed with the heart arrested, there is no effective way to judge the relationship of the border-zone to the optimal apical location. Accordingly, the present device when used with a beating heart is useful in appropriately locating the apex of the heart. In other words, such a device can be considered to be an apex locator. Such a device can be considered to be a systolic-type sizer. On the other hand, if the surgeon decides to reconstruct the left ventricle while the heart is arrested, the sizer can be considered to be a diastolic-type sizer.

As explained above with reference to FIG. 4, a preferred embodiment of the process of the present invention includes using a conventional cardiopulmonary bypass system to oxygenate the patient's blood, according to Step 30. Also, preferably the patient's heart continues to beat, although in some cases it may be advantageous to arrest the beating of the heart using conventional cardioplegic procedures, step 34.

It is important that the volume of the sizer be different when the sizer is used with a beating heart than when it is used with an arrested heart. To appreciate this difference, certain terms should be understood. Systole is the portion of the cardiac cycle in which the ventricle contracts. The degree of contraction is determined by complex factors but is certainly afterload dependent (in that decreased afterload leads to increased contractility and a smaller end-systolic volume relative to conditions of increased afterload). Diastole is the portion of the same cardiac cycle wherein the ventricle reaches its maximum dimension (from a volume standpoint). Unlike systole, which is active, diastole is passive, and is preload dependent; a higher preload will lead to a larger end-diastolic volume than will a lower preload. LVESV is a conventional acronym meaning left ventricular end systolic volume, and LVEDV is a similar acronym meaning left ventricular end diastolic volume. Stroke volume is a conventional phrase meaning the volume of blood expelled by the left ventricle during a single stroke.

In the process of the present embodiment the left ventricle is surgically entered, and therefore circulation is supported by cardiopulmonary bypass or other means. Accordingly, afterload and preload are both zero. Therefore, since diastole is passive, systolic contraction is unopposed, and during systole the ventricular chamber becomes smaller than in any normal physiological state. It is therefore important that the volume of the sizer take this specific aspect of cardiac function into account.

Our preferred device and process device includes two aspects to take this aspect of cardiac function into account. First, the sizer is slightly stiffer than similar devices used in arrested, "diastolic" ventricles to identify the proper size for Left Ventricular Reconstruction. This is because the absence of afterload may result in a hyper-contractile condition in which the systolic dimension would otherwise become undersized. Slightly increased resistance in the device will mitigate against exaggeration of the systolic contraction. Specifically, our preferred systolic-type sizer has a stiffness of about 60-80 durometer Shore A as compared to a stiffness of 40-65 durometer Shore A for our diastolic-type sizer.

Secondly, our preferred systolic-type sizer, while maintaining the long axis dimensions of its "diastolic" counterpart, is smaller in the short axis. The short axis in this context means the diameter measured generally perpendicular to line 93 shown in FIG. 5. The diameter is smaller by an amount that will make the total volume of the sizer the stroke volume less than the corresponding diastolic-type sizer. In other words, this device is the calculated post op LVESV while the arrested device represents the calculated post op LVEDV. A side by side comparison of the two devices would approximate a left-ventriculogram or Echocardiography taken in systole (this device) and diastole (the arrested heart device).

Figure 20:
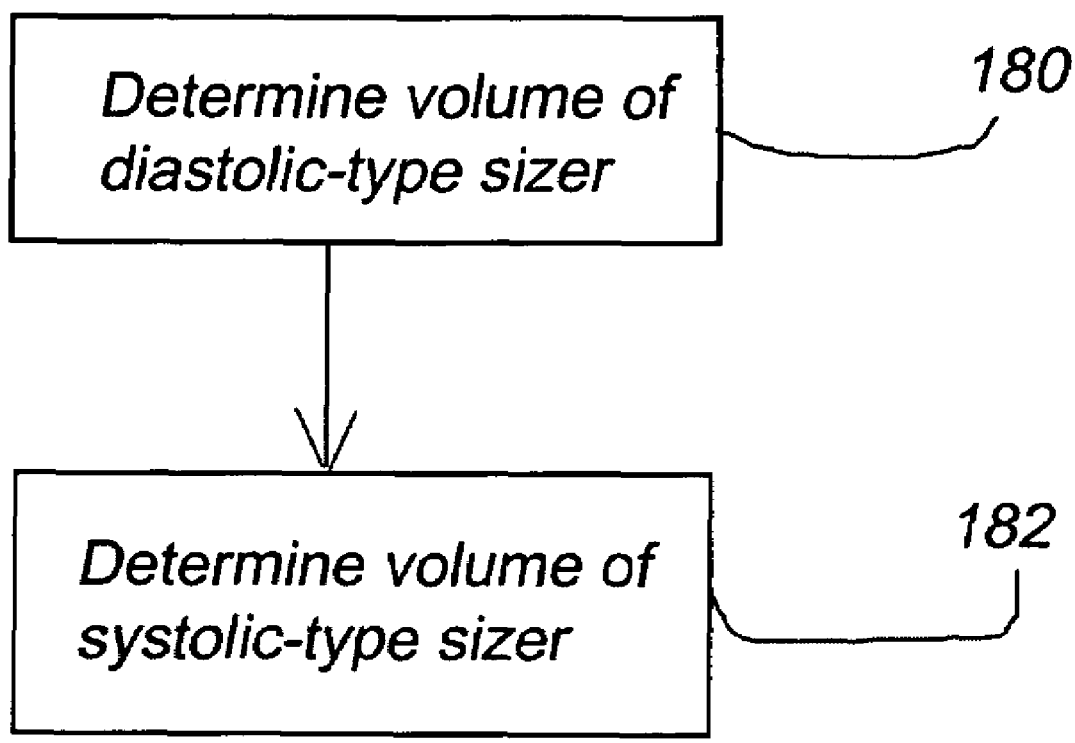
FIG. 20 is a block diagram of a preferred process for determining the size of a systolic-type sizer.

Turning now to FIG. 20 a preferred embodiment of the present process is illustrated. To determine the size of a systolic-type sizer, one first determines the size of a corresponding diastolic-type sizer. This is done, for example, as described above and illustrated in FIG. 17. The result of this calculation is $V_d$, which is the volume of the diastolic-type sizer, and is illustrated as step 180 in FIG. 20. After $V_d$ has been calculated, the volume of the corresponding systolic-type sizer is calculated according to the following formula, step 182:

$$V_s = V_d \times 67\%$$

Where: $V_d$=volume of diastolic-type sizer
$V_s$=volume of systolic-type sizer

For example, if the patient's left ventricle diameter is between 5.18-5.32 cm, and the appropriate diastolic-type sizer is determined to be 120 cc, then if the beating heart procedure is chosen, an 80 cc systolic-type sizer (120 cc×67%) will be used. Otherwise, 120 c diastolic-type sizer will be used for the arrested heart procedure.

We have found that although 67% is the preferred multiplier, in some cases the range for the multiplier can be from 40% to 70%.

What is claimed is:

1. A method for use in reconstructing the left ventricle of the heart of a patient from a diseased state to an appropriate reconstructed state, the method comprising the steps of:

determining the body surface area of the patient;

determining a characteristic of the left ventricle which is the same in the diseased state as in the reconstructed state;

determining an appropriate sizer based on the determined body surface area of the patient and the characteristic of the left ventricle which is the same in the diseased state as in the reconstructed state;

identifying akinetic tissue within a heart chamber wall;

making an incision through the akinetic tissue in the chamber wall;

inserting said appropriate sizer into the chamber through the incision;

removing the sizer; and, closing the incision.

2. A method according to claim 1 wherein the body surface area of the patient is determined based on the height of the patient and the weight of the patient.

3. A method according to claim 1 wherein said step of determining the appropriate sizer further comprises:
- determining a first size of the sizer based on body surface area of the patient
- determining a second size of the sizer based on the characteristic of the left ventricle which is the same in the diseased state as in the reformed state; and,
- determining the volume of the appropriate sizer by selecting the lesser of the first size and the second size.

4. A method for use in reconstructing the left ventricle of the heart of a patient from a diseased state to an appropriate reconstructed state, the method comprising the steps of:
- determining the body surface area of the patient;
- determining the short axis left ventricle diameter at papillary muscle tips of the heart of the patient;
- determining an appropriate sizer based on the determined body surface area of the patient and the short axis left ventricle diameter at papillary muscle tips of the heart of the patient;
- identifying akinetic tissue within a heart chamber wall;
- making an incision through the akinetic tissue in the chamber wall;
- inserting said appropriate sizer into the chamber through the incision;
- removing the sizer; and,
- closing the incision.

5. A method according to claim 4 wherein the body surface area of the patient is determined based on the height of the patient and the weight of the patient.

6. A method according to claim 4 wherein said step of determining the appropriate sizer further comprises:
- determining a first size of the sizer based on body surface area of the patient
- determining a second size, $V_2$, of the sizer based on short axis left ventricle diameter at papillary muscle tips of the heart of the patient; and,
- determining the volume of the appropriate sizer by selecting the lesser of the first size and the second size.

7. A method according to claim 6 wherein said step of determining a second size, $V_2$, of the sizer based on short axis left ventricle diameter at papillary muscle tips, d, of the heart of the patient comprises calculating $V_2$ according to the equation $V_2 = d * X$, where X is a constant.

* * * * *